United States Patent [19]

Vartiak et al.

[11] 4,076,516

[45] Feb. 28, 1978

[54] AQUATIC HERBICIDES

[75] Inventors: Joseph F. Vartiak, Naperville, Ill.; George E. Wortley, Longwood, Fla.

[73] Assignee: Nalco Chemical Company, Oak Brook, Ill.

[21] Appl. No.: 798,411

[22] Filed: May 19, 1977

Related U.S. Application Data

[63] Continuation-in-part of Ser. No. 740,509, Nov. 10, 1976, abandoned.

[51] Int. Cl.² ............................................. A01N 17/00
[52] U.S. Cl. .......................................................... 71/66
[58] Field of Search ............................................ 71/66

[56] References Cited

U.S. PATENT DOCUMENTS

| 3,360,356 | 12/1967 | Vartiak | 71/65 |
| 3,393,990 | 7/1968 | Geary | 71/65 |
| 3,959,237 | 5/1976 | Blank | 71/93 X |

FOREIGN PATENT DOCUMENTS

| 48-10535 | 4/1973 | Japan | 71/DIG. 1 |

*Primary Examiner*—Lewis Gotts
*Assistant Examiner*—Catherine L. Mills
*Attorney, Agent, or Firm*—John G. Premo; Robert A. Miller; Barry W. Sufrin

[57] ABSTRACT

Aquatic herbicides of improved activity are afforded by applying them beneath the surface of waters that contain undesirable aquatic vegetation, said application being performed in the presence of a water-soluble vinyl addition polymer having a molecular weight of at least 10,000.

12 Claims, No Drawings

AQUATIC HERBICIDES

This application is a continuation-in-part of application Ser. No. 740,509 filed Nov. 10, 1976, now abandoned.

INTRODUCTION

Many species of undesirable aquatic vegetation may be contained or controlled by treating this vegetation with a variety of aquatic herbicides. These herbicides are oftentimes applied by spraying them beneath the water's surface. Many of these aquatic herbicides are applied in conjunction with weighting agents such as sugar or as water-in-oil emulsions which are formulated so that the emulsion slowly inverts in the water. The emulsion droplets, prior to inverting, slowly sink to the bottom of the water where they, hopefully, become affixed to the plant or to the bottom of the body of water where their activity can be focused directly against the vegetation sought to be controlled.

The application of aquatic herbicides as described above could be greatly improved if it were possible to combine with these herbicides either as a neat material or, as they are prepared in commercial formulations, a chemical substance which would allow them to attach themselves selectively to aquatic plants when they are applied under the surface of the water.

THE INVENTION

In accordance with the invention, it has been found that aquatic herbicides may be improved in their activity by applying these herbicides under water to the vegetation to be controlled in the presence of a minor amount of a water-soluble vinyl addition polymer which has a molecular weight of at least 10,000.

TYPICAL AQUATIC HERBICIDES

While many aquatic herbicides can be improved in their activity by combining them in accordance with the methods of this invention with the water-soluble polymers, certain herbicides are particularly suited for use. Illustrative of such materials are:

7-Oxabicyclo (2,2,1) heptane-2,3 dicarboxylic acid;
copper—triethanolamine complex; and
copper—ethylenediamine complex.

THE WATER-SOLUBLE POLYMERS

The water-soluble polymers which are useful in this invention have been previously described in numerous publications and patents. The preferred polymers most commonly used in this application are water-soluble polymers and copolymers of acrylic acid and its derivatives. Preferred polymers for use in the practice of this invention include homopolymers of acrylic acid and their water-soluble salts, copolymers of acrylic acid with water-soluble non-ionic monomers such as acrylamide, and homopolymers and copolymers of acrylamide. Preferably, these polymers contain from 5–100 weight percent of acrylic acid and from 0–95% by weight of acrylamide or other water-soluble non-ionic monomers. A particularly useful polymer in the above class is a homopolymer of acrylic acid in the sodium salt form. The acrylic acid in the above material may be present in the acid form or may exist as the alkali metal or ammonium salt thereof. It is preferred in the practice of this invention to use sodium polyacrylate. As will be seen from the above description, by the term "acrylic acid", is also meant other water-soluble materials having a vinyl group and containing a carboxyl group. Examples of monomers of this class include methacrylic acid, and α-hydroxyacrylic acid. As stated above, the acrylic acid or its derivatives may be copolymerized with a non-ionic vinyl addition monomer, preferably acrylamide, but may also be polymerized with any water-soluble non-ionic vinyl addition monomer. These monomers are well known to those skilled in the art and need not be further elaborated on in this specification.

While acrylic acid polymers have been listed above to be the preferred polymeric species in this invention, other various types of water-soluble polymers are known to function in this invention. As a result, we do not wish to be limited to the above compositions but to only those materials which will perform adequately in the course of our invention. For instance, on examining U.S. Pat. No. 3,418,237 and U.S. Pat. Nos. 3,259,370 and 3,171,805, it will be seen that the water-soluble vinyl addition polymers may be either cationic or anionic and, in some instances, the ionic charges will be sufficiently slight so that the polymers may be considered as non-ionic.

For example, water-soluble polymers and copolymers of allyl, diallyl amines, or dimethylaminoethylmethacrylate are cationic. Polymers such as polyacrylamide and polyvinyl alcohol are non-ionic, and polymers such as polyacrylic acid or polystyrene sulfonates are anionic. All of these polymers may be used in the practice of the invention.

The molecular weight of the polymers described above may vary over a wide range, e.g. 10,000–25,000,000. This invention finds its greatest utility in using acrylic acid polymers which have molecular weights in excess of 1 million.

Many of these polymers are in the form of dry, granular materials and can be prepared as dilute aqueous solutions, e.g. 1–2%. A convenient form of these polymers are polymers of the type described in U.S. Pat. No. 3,624,019. This patent discloses that when polymers of the above type are in the form of water-in-oil emulsions, they are capable of being added to water, and under certain conditions, are readily inverted to produce dilute solutions of these polymers in very short periods of time. Thus, it is preferred in this invention for ease of handling and dissolution into polymer that the polymer be contained in a water-in-oil emulsion which can be inverted to cause the solubilization of the polymer when contacted with water. Since oil is the continuous phase of these emulsions, it renders them compatible with herbicides which are normally applied or shipped as oil solutions or suspensions.

Another useful class of polymeric materials suitable for the practice of this invention are solutions of polyethylene oxide. These materials are generally commercially available and are marketed by the Union Carbide Corporation under the Trademark "Polyox". The molecular weight of the polyethylene oxide useful in the practice of this invention ranges from about 100,000 to 5 million or higher. All that is important is that this material be of a relatively high molecular weight and be water soluble.

UTILIZING THE WATER-SOLUBLE POLYMERS

WITH THE AQUATIC HERBICIDES

The water-soluble polymers used in the practice of the invention may be employed in conjunction with the aquatic herbicides in a variety of ways. In one of its simplest forms, the aquatic herbicide would be applied below the surface of the water through a plurality of injection nozzles. The polymer in the form of a concentrated liquid would be metered into the herbicide pump, where it is mixed with the herbicide just prior to where the feed line goes into the application nozzles. In another embodiment of the invention, the polymers may be compatible with the particular herbicidal formulation used and can be directly admixed therewith. In some instances, it is beneficial if the polymer is injected below the surface of the water concurrently with the herbicide.

One of the common modes of applying certain water-soluble aquatic herbicides is to prepare them in the form of a water-in-oil emulsion which slowly inverts and attaches particles of the herbicide to the aquatic weed sought to be treated. These formulas are so prepared as to allow the emulsion droplets to slowly sink and attach themselves to the plant or its growth situs prior to inversion. Emulsions of this type, while having met with some success, are difficult to formulate and handle and are relatively unpredictable with respect to their stability once applied. The use of the polymers of this invention improve the applicational technique of these herbicides.

The polymers of the invention, when used in accordance with the teachings hereof, particularly when applied under conditions of good agitation, then to encapsulate the active herbicide, carry it down to the surface of the vegetation and its growth situs, and allow it to be released at a fairly uniform rate, thereby achieving maximum killing or control. Without the use of these polymers, many of the herbicides are sufficiently dissipated after being injected into the water where much of the active ingredient does not contact the vegetation, thereby having little or no effect with respect to the control and irradication of undesirable aquatic vegetation.

The amount of polymer used to achieve the results of this invention may be varied. The particular amount of material utilized will depend upon the particular polymer used, the molecular weight of the polymer, the mode of application, the particular aquatic herbicide with which it is combined, and, of course, the amount of herbicidal material being sprayed per unit of area. Field tests have shown that fairly good control is achieved when the polymer is applied along with the herbicide in a dosage range of 0.005–0.2 pounds of the water-soluble polymer per gallon of solution sprayed. Preferably, from 0.01–0.1 pounds of polymer per gallon are used, and, most preferably, from 0.02–0.075 pounds per gallon of solution are utilized. In the preferred practice of this invention, water-in-oil emulsions of the vinyl addition polymer are utilized. These emulsions are commercially available and generally have polymer concentrations of approximately 10–35% by weight. These materials have been successfully used as the following examples show, at a rate of approximately 1.5 gallons of 30% latex per 100 gallons of spray solution which translates to roughly .038 pounds of active polymer per gallon of sprayed solution.

In order to further illustrate the instant invention, the following examples are presented:

EXAMPLE I

The particular herbicide used in this test was a commercial herbicide which contained 10.4% by weight of 7-oxabicyclo (2,2,1) heptane-2,3 dicarboxylic acid. It would be used for controlling hydrilla growing in a small Florida lake. One acre plots would be applied using commercial spray equipment with the material being injected under water with small high pressure nozzoles. The polymers would be fed before the mixing pump. The amount of the herbicide applied would be 4 gallons per acre which would be diluted to 25 gallons per acre to accommodate blending with the polymers. The results of these tests are shown below in Table I.

TABLE I

| Plot | Adjuvant | Dosage | 15-Day Reading |
|---|---|---|---|
| 1 | Polyacrylamide[1] | .038 lbs./gal. | 90–100% Kill |
| 2 | Polyacrylamide[1] | .076 lbs./gal. | 90–100% Kill |
| 3 | Acrylamide-Na acrylate[2] | .0129 lbs./gal. | 90–100% Kill |
| 4 | Acrylamide-Na acrylate[2] | 0.38 lbs./gal. | 90–100% Kill |
| 5 | Sodium Acrylate[3] | 0.516 lbs./gal. | 90–100% Kill |
| 6 | Sodium Acrylate[3] | 0.129 lbs./gal. | 90–100% Kill |
| 7 | Control (No Adjuvant) | — | 50% Kill |

[1] A water-in-oil emulsion of polyacrylamide containing 30% by weight polymer having an intrinsic viscosity of approximately 17.
[2] A water-in-oil emulsion of an acrylamide (70%)-sodium acrylate (30%) copolymer containing 30% by weight of the copolymer having an intrinsic viscosity of approximately 19.
[3] A water-in-oil emulsion of sodium polyacrylate containing 30% by weight polymer and having an intrinsic viscosity of approximately 20.

EXAMPLE II

The particular herbicide employed in this test was a commercial product containing 6,7-dihydrodipyrido (1,2-a.2',1'-C) pyrazinediium bromide Ortho ® Diquat, a composition available from the Chevron Chemical Company and Komeen ® an ethylenediamine copper complex containing approximately 8% elemental copper from Sandoz Incorporated. The material was sprayed at a level of 100 gallons per acre, each 100 gallons containing 2 gallons of Diquat and 4 gallons of Komeen. Spraying was conducted at 5 gallons per minute through a line beneath the surface of the water. The plot sprayed was located in the extreme southern portion of the United States in a canal heavily infested with Hydrilla weeds. Water temperature was 64° F, and the Hydrillas were 3–4" below the surface area in most areas of the canal with an estimated 65–85% of the area being infested with the weed. A one acre plot was treated as above to serve as the control.

Using the same technique, 1.5 gallons of a water-in-oil emulsion containing 30% by weight sodium polyacrylate having a molecular weight of approximately 2 million, was added on the suction side of the spray pump per 100 gallons of spray solution. In addition, 170 milliliters of an hydrophilic emulsifier was added incrementally with the polymer emulsion so as to enable it to invert when applied. The 1.5 gallons of water-in-oil emulsion translates to roughly 0.038 lbs. of polymer per each gallon of material sprayed.

Approximately one month later, plots applied were examined. As the treated plot areas were approached from a distance, the specifically treated plot areas could readily be seen. The treated plots showed definite burn and kill on the top with the Hydrilla being loose and decomposing. All plots including the control had this appearance. Upon looking into the water, it could be seen that the Hydrilla had been dropped by approximately one foot with a kill. By comparing pulled Hydrilla from treated and untreated areas, it was noted that the treated Hydrilla had a fair amount of yellow stems and defoliation which indicated herbicidal effect 3–4 feet below the surface as well as on the top. This was in contrast to the plots not so treated where this was not evident at this level below the surface. The treated plots indicated that excellent coverage of the herbicide had been achieved with no spreading of the herbicide outside the given plots.

Based on the above results, it is evident that the polymeric adjuvant of this invention provides an improved method for the suppression of aquatic weeds. The polymer adjuvant of this invention being completely water-soluble does not cause the harm of using inverted oil emulsions and provides much more effective control of aquatic weeds than the herbicidal solution alone.

EXAMPLE III

In another Florida fresh water lake, Hydrilla was treated with inverts of two herbicides, and with polymer solutions of the two herbicides. The application was made beneath the surface of the water. The results of these tests are set forth below in Table II.

TABLE II

| Plot | Herbicidal Treatment/Acre | Lbs. Polymer[3] Gal. Sprayed Solution | Two Week Results % of Kill |
|---|---|---|---|
| 1 | 2 gal. Diquat[1]<br>4 gal. Komeen[2] | [4] | 10% |
| 2 | 2 gal. Diquat<br>4 gal. Komeen | .043 | 25% |
| 3 | 2 gal. Diquat<br>4 gal. Komeen | .077 | 0% |
| 4 | 2 gal. Diquat<br>4 gal. Komeen | .051 | 15–20% |
| 5 | 8 gal. Komeen | .051 | 75% |
| 6 | 8 gal. Komeen | [4] | 5% |
| 7 | 6 gal. Komeen | [4] | 30% |
| 8 | 6 gal. Komeen | .0645 | 70% |

[1] 6,7-dihydrodipyrido (1,2-a:2',1'-C) pyrazinediium bromide.
[2] Copper, ethylenediamine complex.
[3] Water-in-oil emulsion containing 30% by weight of an acrylamide-acrylic acid copolymer, 30% acrylic acid sodium salt.
[4] A commercially available invert treatment.

EXAMPLE IV

A herbicidal mixture would be prepared containing 4 gallons per 100 gallons of Diquat and 8 gallons per 100 gallons of Komeen. To this solution would be added 1.0 lbs. of a polyethylene oxide having an approximate molecular weight of 4 million dissolved in an alcohol-water solution. After stirring, the mixture would be diluted to 200 gallons and would be sprayed onto Hydrilla located below the surface of the water by a mechanism located below the surface of the water at a rate of approximately 60 gallons of herbicide solution per acre. After inspecting the resultant sprayed area, at periods of 3, 6, and 9 weeks, an approximate 85% kill of Hydrilla would be noted, with areas not so treated not being affected. The resultant polymer treated plots would have a higher kill of Hydrilla than those plots treated with the same amount of herbicide not containing the polymer.

Having thus described our invention what is claimed is as follows:

1. A process for improving the activity of aquatic herbicides which comprises applying these herbicides under water to the vegetation to be controlled in the presence of a minor amount of a water soluble acrylic acid polymer which has a molecular weight of at least 10,000.

2. The process of claim 1 wherein the water soluble acrylic acid polymer is an acrylic acid-acrylamide copolymer.

3. The process of claim 1 wherein the water soluble acrylic acid polymer is employed at a level of from 0.005–0.2 lbs. of polymer per gallon of herbicidal solution.

4. The process of claim 1 wherein the vegetation to be controlled is Hydrilla.

5. The process of claim 1 wherein the water soluble acrylic acid polymer is contained in a water-in-oil emulsion which is inverted to cause the solubilization of the polymer when contacted with water.

6. A process for improving the activity of aquatic herbicides which comprises applying the herbicide under water to the vegetation to be controlled in the presence of from 0.01–0.1 lbs. of a water soluble acrylic acid polymer per gallon of herbicidal solution, said polymer having a molecular weight of at least 10,000.

7. The process of claim 6 wherein the water soluble acrylic acid polymer is a homopolymer of polyacrylic acid in the sodium salt form having a molecular weight of approximately 2 million.

8. The process of claim 6 wherein the water soluble acrylic acid polymer is a copolymer of acrylic acid and acrylamide.

9. The process for improving the activity of aquatic herbicides which comprises applying these herbicides under water to the vegetation to be controlled in the presence of a minor amount of a solution of polyethylene oxide which has a molecular weight of from 100,000 to 5 million.

10. The process of claim 1 wherein the water soluble acrylic acid polymer is a homopolymer of polyacrylic acid in the sodium salt form having a molecular weight of approximately 2 million.

11. The process of claim 1 wherein the aquatic herbicide is a member of the group consisting of 6,7-dihydrodipyrido (1.2–a.2',1'–C) pyrazinediium bromide, ethylene diamine copper complex, 7-oxabicyclo (2,2,1) heptane-2,3 dicarboxylic acid.

12. The process of claim 11 wherein the vegetation to be controlled is hydrilla.

* * * * *